US008034801B2

(12) United States Patent
Hamura et al.

(10) Patent No.: US 8,034,801 B2
(45) Date of Patent: Oct. 11, 2011

(54) ANALGESIC AGENT

(75) Inventors: Hiroki Hamura, Hamura (JP); Kenji Shimizu, Hamura (JP); Hashime Kanazawa, Hamura (JP)

(73) Assignee: Aska Pharmaceutical Co., Ltd., Tokyo (JP)

( * ) Notice: Subject to any disclaimer, the term of this patent is extended or adjusted under 35 U.S.C. 154(b) by 59 days.

(21) Appl. No.: 12/309,180

(22) PCT Filed: Jul. 12, 2006

(86) PCT No.: PCT/JP2006/313856
§ 371 (c)(1),
(2), (4) Date: Jan. 9, 2009

(87) PCT Pub. No.: WO2008/007426
PCT Pub. Date: Jan. 17, 2008

(65) Prior Publication Data
US 2009/0253729 A1 Oct. 8, 2009

(51) Int. Cl.
*A01N 37/18* (2006.01)
*A01N 57/00* (2006.01)
(52) U.S. Cl. .................................. 514/183; 514/616
(58) Field of Classification Search .............. 514/183
See application file for complete search history.

(56) References Cited

U.S. PATENT DOCUMENTS
2006/0134106 A1 6/2006 Adair

FOREIGN PATENT DOCUMENTS

| EP | 0 896 815 | 2/1999 |
| JP | 5-194227 | 8/1993 |
| JP | 10-504557 | 5/1998 |
| JP | 11-512081 | 10/1999 |
| JP | 2003-535833 | 12/2003 |
| WO | 96/05834 | 2/1996 |
| WO | 97/04780 | 2/1997 |
| WO | 01/93852 | 12/2001 |

OTHER PUBLICATIONS

Palangio et al. (Combination Hydrocodone and Ibuprofen Versus Combination Codeine and Acetaminophen for the Treatment of Chronic Pain), Clinical Therapeutics/ vol. 22, No. 7, 2000.*

International Search Report issued Oct. 25, 2006 in the International (PCT) Application of which the present application is the U.S. National Stage.
Y. Shima et al., "Totsu Management no Kihon to Jissai", Mediina, 2005, vol. 42, No. 11, pp. 2005-2009 (with translation).
M. Fukushima, "Merck Manual Dai 17 Han Nihongoban", Nikkei Business Publications, Inc., Dec. 10, 1999, pp. 1367-1379.
M. Palangio et al., "Combination Hydrocodone and Ibuprofen Versus Combination Codeine and Acetaminophen for the Treatment of Chronic Pain", Clinical Therapeutics, vol. 22, No. 7, pp. 879-892, 2000.
H. Ueda, Folia Pharmacol. Jp., (Nippon Yakurigaku Zasshi) vol. 122, pp. 192-200, 2003.
Supplementary European Search Report dated Oct. 28, 2009 in European Application No. EP 06 76 8120.
Japanese Office Action issued May 31, 2011 in Japanese Application No. 2005-154597.
Tetsushi Fukushige, Japanese Journal of Clinical and Experimental Medicine, 2003, vol. 80 No. 7, pp. 1283-1288, with partial English translation.
Yoshikazu Chinone, Modern Physician, 2003, vol. 23 No. 3, pp. 323-326, with partial English translation.

* cited by examiner

*Primary Examiner* — Sreeni Padmanabhan
*Assistant Examiner* — Timothy E Betton
(74) *Attorney, Agent, or Firm* — Wenderoth, Lind & Ponack, L.L.P.

(57) ABSTRACT

A pharmaceutical preparation useful for alleviating or treating a pain, e.g., a chronic pain (particularly, a neuropathic pain) is provided. The pharmaceutical preparation contains (a) a propionic acid-derived nonsteroidal anti-inflammatory agent (e.g., ibuprofen), (b) a non-pyrazolone antipyretic analgesic agent (e.g., acetaminophen), and (c) an opioid analgesic agent (e.g., codeine phosphate, dihydrocodeine phosphate). The pharmaceutical preparation may contain 5 to 100 parts by weight of the antipyretic analgesic agent (b) or 0.5 to 500 parts by weight of the analgesic agent (c) relative to 100 parts by weight of the anti-inflammatory agent (a). The pharmaceutical preparation may be substantially free from a non-toxic N-methyl-D-aspartate receptor antagonist and may contain 20 to 80 parts by weight of the antipyretic analgesic agent (b) and 1 to 100 parts by weight of the analgesic agent (c) relative to 100 parts by weight of the anti-inflammatory agent (a).

5 Claims, 1 Drawing Sheet

ANALGESIC AGENT

This application is a U.S. national stage of International Application No. PCT/JP2006/313856 filed Jul. 12, 2006.

TECHNICAL FIELD

The present invention relates to a pharmaceutical preparation useful for alleviating (or mitigating) or treating a pain, for example, a chronic pain (particularly, a neuropathic pain).

BACKGROUND ART

Immediately alleviating a pain of which a patient with a disease or disorder complains is most important to most of the treatment for the disease or disorder in terms of the mitigation of the patient's physical pain as well as mental anguish. Pain is usually classified into acute pain and chronic pain. The acute pain results from a tissue damage caused by a stimulation such as a mechanical stimulus or heat. Heretofore, all of analgesic agents have been developed with the aim of alleviating the acute pain. The chronic pain means that a pain continuing for 6 or more months, which appears after a recovery of a tissue damage resulting in acute pain or due to lumbago, migraine, arthritis, cancer, and other factors and hinders patient's daily life, or which results from an unknown origin. Moreover, pain is classified into four categories according to the cause: nociceptive, inflammatory, neuropathic (or neurogenic), and psychogenic pains. These pains are treated depending on the respective causes thereof. For example, the invasive pain can completely subside by morphine or the like. The inflammatory pain can cease after inhibition or elimination of the cause using an anti-inflammatory agent. However, it is difficult to remove the neuropathic pain since the cause of the pain is specific. Specifically, the cause of the neuropathic pain is a temporary injury to the nervous system or an abnormal function of the nervous system. That is, the nerve itself has a trouble, and the plasticity in the nervous system becomes chronic. In addition, since the chronic pain induces a new plastic change in the neural circuit, it is difficult to remit the symptom, to say nothing of the cause. The neuropathic pain is a pain as represented by a sensuous expression such as "numbness" or "a shooting pain" and is also a continuous or sudden pain. Moreover, the neuropathic pain is known for its resistance to an antiphlogistic analgesic agent or a narcotic analgesic agent.

The effective method for treating the neuropathic pain includes, for example, methods described in Folia Pharmacol. Jpn., 122, 192-200 (2003) (Non-patent Document 1). In this document, treatments with an α2 adrenergic receptor antagonist, a sodium receptor antagonist, a capsaicin cream, a TrkB receptor inhibitor, or an Rho inhibitor have been examined.

Moreover, Japanese Patent Application Laid-Open No. 535833/2003 (JP-2003-535833A, Patent Document 1) discloses that a pharmaceutical composition containing a kappa-opioid (nalbuphine) and an opioid antagonist (naloxone, naltrexone, nalmefene) is useful for treating a pain including both inflammatory and neuropathic pains. Incidentally, the document does not disclose that a propionic acid-derived nonsteroidal anti-inflammatory agent and a non-pyrazolone antipyretic analgesic agent is further added or mixed to or with the pharmaceutical composition.

Further, Japanese Patent Application Laid-Open No. 512081/1999 (JP-11-512081A, Patent Document 2) discloses that a pharmaceutical composition containing an opioid analgesic agent (such as codeine or dihydrocodeine) as a first component, a nonopioid analgesic agent (such as acetaminophen or ibuprofen) as a second component, an N-methyl-D-aspartate receptor antagonist (such as dextromethorphan) as a third component is useful for treating an acute or chronic pain (e.g., arthritic pain, lumbosacral, musculoskeletal pain, post-operative pain, and headache).

As described above, a variety of treatments for pain has been carried out. However, preparations or treatment methods which enable more effective alleviation and treatment for pain is desired still now. In particular, there are few reports concerning effective treatment methods for a neuropathic pain, which is one of chronic pains, and the development of methods for treating the neuropathic pain effectively has been desired.

[Patent Document 1] JP-2003-535833A (Claims 1, 8, and 9, paragraph number [0002])

[Patent Document 2] JP-11-512081A (Claims 1 and 15, page 8, lines 27-28 of Specification)

[Non-patent Document 1] Folia Pharmacol. Jpn. 122, 192-200 (2003), attributed to Ueda Hiroshi

DISCLOSURE OF THE INVENTION

Problems to be Solved by the Invention

It is therefore an object of the present invention to provide a pharmaceutical preparation (an analgesic agent) useful for alleviating or treating a pain, for example, a chronic pain (particularly, a neuropathic pain), effectively.

Another object of the present invention is to provide a pharmaceutical preparation useful for treating a disease with a neuropathic pain and a neuropathic pain thereof (for example, carcinomatous pain, postherpetic neuralgia, post-thoracotomy pain, trigeminal neuralgia, phantom limb pain, causalgia, diabetic neuropathic pain, and injury or amputation of limb).

Means to Solve the Problems

The inventors of the present invention made intensive studies to achieve the above objects and finally found that combination of a propionic acid-derived nonsteroidal anti-inflammatory agent, a non-pyrazolone antipyretic analgesic agent, and an opioid analgesic agent potentiates the analgesic effect of the opioid analgesic agent, whereby even a neuropathic pain is effectively alleviated. The present invention was accomplished based on the above findings.

That is, the pharmaceutical preparation of the present invention contains a propionic acid-derived nonsteroidal anti-inflammatory agent (or a propionic acid-derivative nonsteroidal anti-inflammatory agent), a non-pyrazolone antipyretic analgesic agent, and an opioid analgesic agent. The proportion of the non-pyrazolone antipyretic analgesic agent may be about 5 to 100 parts by weight relative to 100 parts by weight of the propionic acid-derived nonsteroidal anti-inflammatory agent. The proportion of the opioid analgesic agent may be about 0.5 to 500 parts by weight relative to 100 parts by weight of the propionic acid-derived nonsteroidal anti-inflammatory agent. The proportion of the opioid analgesic agent may be about 1 to 1000 parts by weight relative to 100 parts by weight of the non-pyrazolone antipyretic analgesic agent. The pharmaceutical preparation of the present invention may be substantially free from a nontoxic N-methyl-D-aspartate receptor antagonist, and may contain about 20 to 80 parts by weight of the non-pyrazolone antipyretic analgesic agent and about 1 to 100 parts by weight of the opioid analgesic agent relative to 100 parts by weight of the propionic acid-derived nonsteroidal anti-inflammatory agent.

The propionic acid-derived nonsteroidal anti-inflammatory agent to be used may include at least one member selected from the group consisting of ibuprofen, ketoprofen, flurbiprofen, flurbiprofen axetil, oxaprozin, fenoprofen, tiaprofenic acid, naproxen, pranoprofen, loxoprofen, alminoprofen, zaltoprofen, and a salt thereof. At least one member selected from the group consisting of acetaminophen, dimetotiazine mesilate, and a salt thereof may be used as the non-pyrazolone antipyretic analgesic agent. The opioid analgesic agent may include at least one member selected from the group consisting of alfentanil, morphine, heroin, levorphanol, hydromorphone, oxymorphone, levellorphan, fentanyl, safentanyl, methadone, meperidine, cocaine, codeine, codeine phosphate, dihydrocodeine, dihydrocodeine phosphate, oxycodone, drocode, tramadol, nalbuphine, nalmefene, nalorphine, naloxone, naltrexone, hydrocodone, hydromorphone, propoxyphene, buprenorphine, butorphanol, pentazocine, and a salt thereof. Among them, for example, ibuprofen as the propionic acid-derived nonsteroidal anti-inflammatory agent, acetaminophen as the non-pyrazolone antipyretic analgesic agent, and codeine phosphate and/or dihydrocodeine phosphate as the opioid analgesic agent may be combined.

The pharmaceutical preparation of the present invention is useful for alleviating (or mitigating) or treating a pain, for example, a chronic pain (particularly, a neuropathic pain) effectively.

Moreover, the pharmaceutical preparation of the present invention is used for alleviating or treating a neuropathic pain, contains substantially no nontoxic N-methyl-D-aspartate receptor antagonist, and contains a propionic acid-derived nonsteroidal anti-inflammatory agent, a non-pyrazolone antipyretic analgesic agent, and an opioid analgesic agent.

Effects of the Invention

The pharmaceutical preparation (pharmaceutical composition) of the present invention can treat or alleviate patient's pain, for example, a chronic pain (particularly, an intractable neuropathic pain) since in the pharmaceutical preparation the propionic acid-derived nonsteroidal anti-inflammatory agent and the non-pyrazolone antipyretic analgesic agent potentiates the analgesic effect of the opioid analgesic agent. Further, the pharmaceutical preparation of the present invention is also useful for treating or curing a neuropathic pain and a disease therewith, for example, carcinomatous pain, postherpetic neuralgia, post-thoracotomy pain, trigeminal neuralgia, phantom limb pain, causalgia, diabetic neuropathic pain, and injury or amputation of limb.

Figure 1:
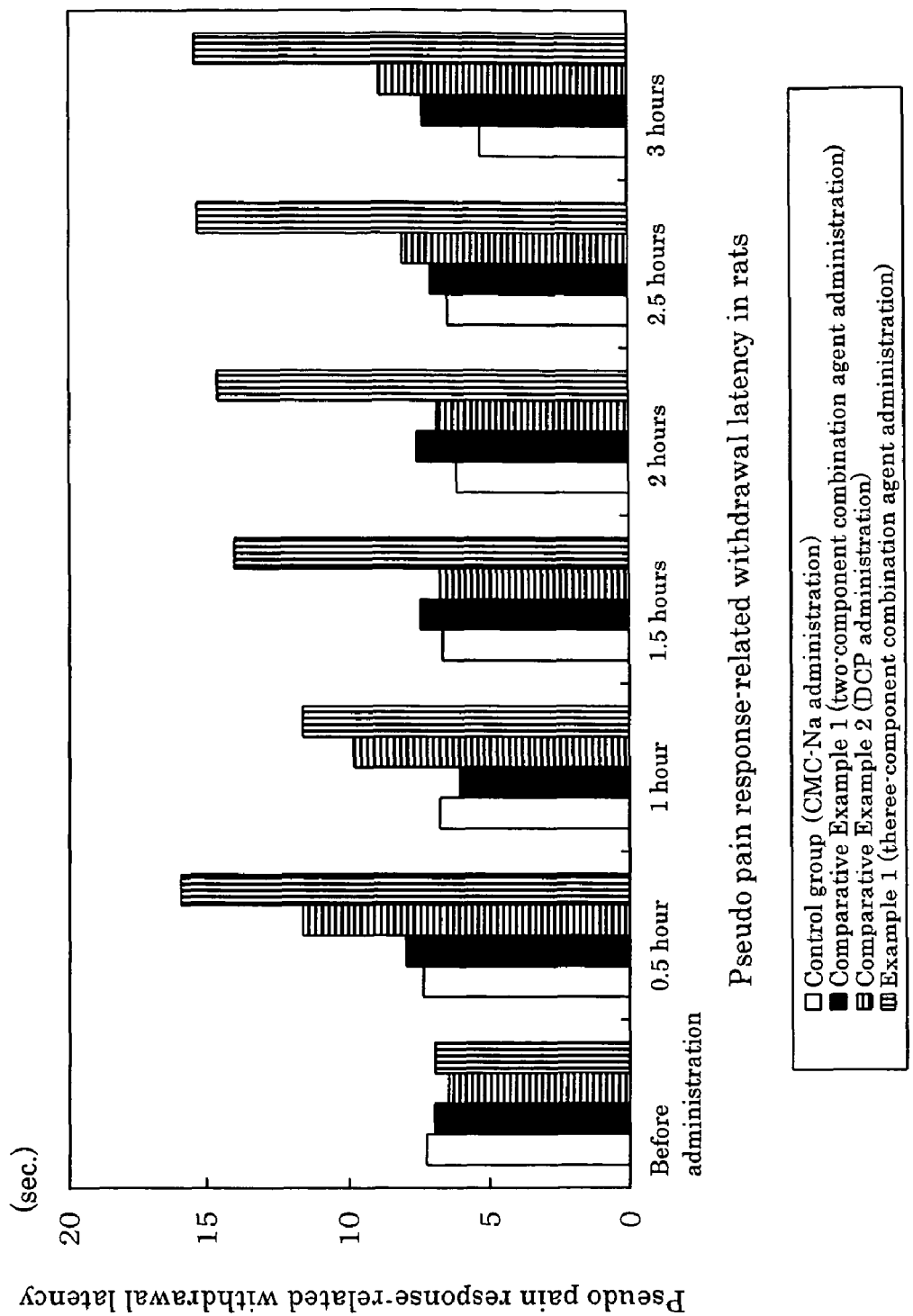
FIG. 1 is a graph showing a change with passage of time of a pseudo pain response-related latent period in Test Example 1.

DETAILED DESCRIPTION OF THE INVENTION (Pharmaceutical Preparation)

The pharmaceutical preparation of the present invention contains (a) a propionic acid-derived nonsteroidal anti-inflammatory agent, (b) a non-pyrazolone antipyretic analgesic agent, and (c) an opioid analgesic agent. The propionic acid-derived nonsteroidal anti-inflammatory agent (a) and the non-pyrazolone antipyretic analgesic agent (b) act as potentiators for the opioid analgesic agent (c) and potentiate the analgesic effect of the opioid analgesic agent (c).

(Propionic Acid-Derived Nonsteroidal Anti-Inflammatory Agent (a))

The propionic acid-derived nonsteroidal anti-inflammatory agent (hereinafter, sometimes abbreviated as the anti-inflammatory agent (a)) means a compound which is one of nonsteroidal anti-inflammatory agents and is derived from propionic acid. Examples of the anti-inflammatory agent (a) may include ibuprofen, ketoprofen, flurbiprofen, flurbiprofenaxetil, oxaprozin, fenoprofen, tiaprofenic acid, naproxen, pranoprofen, loxoprofen, alminoprofen, zaltoprofen, a prodrug thereof, a salt thereof, and others. These anti-inflammatory agents (a) may be used singly or in combination. The preferred anti-inflammatory agent (a) includes ibuprofen. Ibuprofen is a substance having a chemical name, 2-(4-isobutylphenyl)propionic acid, and is an active ingredient contained in the Japanese Pharmacopoeia the 14$^{th}$ edition (hereinafter, referred to as the "Japanese Pharmacopoeia") and the like.

(Non-Pyrazolone Antipyretic Analgesic (b))

The non-pyrazolone antipyretic analgesic agent (hereinafter, sometimes abbreviated as the antipyretic analgesic (b)) may include acetaminophen, dimetotiazine mesilate, a prodrug thereof, a salt thereof, and others. These antipyretic analgesic agents (b) may be used singly or in combination. The preferred antipyretic analgesic agent (b) includes acetaminophen. Acetaminophen is a substance having a chemical name, N-(4-hydroxyphenyl)acetamide, and is an active ingredient contained in the Japanese Pharmacopoeia and the like.

In the pharmaceutical preparation of the present invention, the proportion of the non-pyrazolone antipyretic analgesic agent (b) (for example, acetaminophen) relative to 100 parts by weight of the propionic acid-derived nonsteroidal anti-inflammatory agent (a) (for example, ibuprofen) is not particularly limited to a specific one as long as the proportion is selected from the range of 5 to 100 parts by weight. The proportion is usually about 10 to 90 parts by weight (e.g., about 20 to 80 parts by weight), preferably about 30 to 70 parts by weight (e.g., about 35 to 65 parts by weight), more preferably about 40 to 60 parts by weight (e.g., about 45 to 55 parts by weight), and particularly preferably about 40 to 50 parts by weight.

(Opioid Analgesic Agent (c))

The opioid analgesic agent (hereinafter, sometimes abbreviated as the analgesic agent (c)) may include alfentanil, morphine, heroin, levorphanol, hydromorphone, oxymorphone, levellorphan, fentanyl, safentanyl, methadone, meperidine, cocaine, codeine, codeinephosphate, dihydrocodeine, dihydrocodeine phosphate, oxycodone, drocode, tramadol, nalbuphine, nalmefene, nalorphine, naloxone, naltrexone, hydrocodone, hydromorphone, propoxyphene, buprenorphine, butorphanol, pentazocine, a prodrug thereof, a salt thereof, and others. These analgesic agents (c) may be used singly or in combination. The preferred analgesic agent (c) includes codeine phosphate and dihydrocodeine phosphate. Codeine phosphate is a substance having a chemical name, (5R,6S)-7,8-didehydro-4,5-epoxy-3-methoxy-17-methylmorphinan-6-ol monophosphate hemihydrate, and dihydrocodeine phosphate is a substance having a chemical name, (5R,6S)-4,5-epoxy-3-methoxy-17-methylmorphinan-6-ol monophosphate. Both substances are active ingredients contained in the Japanese Pharmacopoeia and the like.

The proportion of the opioid analgesic agent (c) (for example, at least one member selected from the group consisting of codeine phosphate and dihydrocodeine phosphate) relative to 100 parts by weight of the propionic acid-derived nonsteroidal anti-inflammatory agent (a) (for example, ibuprofen) is not particularly limited to a specific one as long as the proportion is selected from the range of 0.5 to 500 parts by weight. The proportion is usually about 1 to 500 parts by weight (e.g., about 2 to 300 parts by weight), preferably about 1 to 400 parts by weight (e.g., about 3 to 200 parts by weight), more preferably about 1 to 100 parts by weight (e.g., about 5 to 50 parts by weight), and particularly preferably about 3 to 40 parts by weight (e.g., about 5 to 30 parts by weight).

The proportion of the opioid analgesic agent (c) (for example, at least one member selected from the group consisting of codeine phosphate and dihydrocodeine phosphate) relative to 100 parts by weight of the non-pyrazolone antipyretic analgesic (b) (for example, acetaminophen) may be, for example, about 1 to 1000 parts by weight (e.g., about 2 to 500 parts by weight), preferably about 3 to 200 parts by weight (e.g., about 5 to 100 parts by weight), and more preferably about 4 to 150 parts by weight (e.g., about 10 to 75 parts by weight).

A combination of the above-mentioned active ingredients (the anti-inflammatory agent (a), the antipyretic analgesic agent (b), and the analgesic agent (c)) in the present invention is not particularly limited to a specific one. Each active ingredient of the combination may be a compound or a plurality of compounds selected from the examples mentioned above. In particular, the following combination is preferred: a combination of ibuprofen as the anti-inflammatory agent (a), acetaminophen as the antipyretic analgesic agent (b), and codeine phosphate and/or dihydrocodeine phosphate as the analgesic agent (c).

The anti-inflammatory agent (a), antipyretic analgesic agent (b), and analgesic agent (c) may include a mode of an optical isomer (for example, R-body and S-body) or a mode of a mixture of the isomer(for example, a racemic body, an enantiomer mixture, and a diastereomer mixture). The above-mentioned proportion means a proportion of the anti-inflammatory agent (a), the antipyretic analgesic agent (b), and the analgesic agent (c) which are not optically resolved (are racemic bodies). Therefore, use of a pharmaceutically active optical isomer needs an adjustment of the above-mentioned proportion. For example, in the case of use of a pharmaceutically active optical isomer of ibuprofen (e.g., S-ibuprofen) instead of a racemic body of ibuprofen as the anti-inflammatory agent (a), 0.5 part by weight of the optical isomer corresponds to 1 part by weight of the racemic body of ibuprofen. Accordingly, in the case of use of S-ibuprofen as the anti-inflammatory agent (a), the proportion of the antipyretic analgesic agent (b) relative to the anti-inflammatory agent (a) and that of the analgesic agent (c) relative to the anti-inflammatory agent (a) correspond to about twice of the above-mentioned ranges, respectively.

A variety of physiologically or pharmaceutically acceptable salts may be used as the salts of the above-mentioned active ingredients (the anti-inflammatory agent (a), the antipyretic analgesic agent (b), and the analgesic agent (c)). An acid or base forming the salt may be selected according to the species of these active ingredients. These salts may include, for example, an inorganic acid salt (e.g., a salt with an acid such as hydrochloric acid, hydrobromic acid, sulfuric acid, nitric acid, or phosphoric acid); an organic acid salt [for example, a salt with a carboxylic acid {e.g., a salt with a monocarboxylic acid (e.g., a salt with an acid such as oxalic acid, acetic acid, trichloroacetic acid, or trifluoroacetic acid), a polycarboxylic acid salt (e.g., a salt with an acid such as succinic acid, maleic acid, or fumaric acid), and a hydroxycarboxylic acid salt (e.g., a salt with an acid such as tartaric acid, citric acid, lactic acid, gluconic acid, salicylic acid, phenolphthalin, or tannic acid)}, an amino acid salt (e.g., aspartate), and an organic sulfonic acid salt {e.g., a salt of an alkanesulfonic acid (e.g., a salt of an acid such as methanesulfonic acid or ethanesulfonic acid), and an arenesulfonic acid salt (e.g., a salt of an acid such as benzenesulfonic acid, toluenesulfonic acid, or diphenyldisulfonic acid)}]; a salt of an inorganic base [for example, a salt of an alkali metal hydroxide (e.g., a salt of a hydrate such as sodium hydroxide or potassium hydroxide), an alkali metal carbonate, a salt of an alkaline earth metal hydroxide (e.g., a salt of a hydroxide such as calcium hydroxide or magnesium hydroxide), an alkaline earth metal carbonate, an aluminum salt, and an ammonium salt]; and a salt of an organic base [for example, an alkylamine salt (e.g., a trimethylamine salt and a triethylamine salt), an alkanolamine salt (e.g., a monoethanolamine salt and a triethanolamine salt), a polyamine salt such as an alkylenediamine, and a tertiary amine salt such as a pyridine salt].

Moreover, the anti-inflammatory agent (a), the antipyretic analgesic agent (b), and the analgesic agent (c) also include a hydrous compound (or a hydrate) in addition to the physiologically or pharmaceutically acceptable salt.

(Other Active Ingredients)

In addition to the above-mentioned anti-inflammatory agent (a), antipyretic analgesic agent (b), and analgesic agent (c), the pharmaceutical preparation of the present invention may suitably contain other active ingredients which can be added to an analgesic agent. The active ingredient is not particularly limited to a specific one as long as the active ingredient has no adverse effect on the analgesic effects and safety of the pharmaceutical preparation of the present invention. Incidentally, the pharmaceutical preparation of the present invention usually contains substantially no nontoxic N-methyl-D-aspartate (NMDA) receptor antagonist (particularly, dextromethorphan or a salt thereof).

The NMDA receptor includes all of the binding site subcategories associated with the NMDA receptor (for example, the glycine-biding site and the phenylcyclidine (PCP)-binding site), and the NMDA channel (for example, the magnesium channel and the calcium channel). The nontoxic NMDA receptor antagonist means a nontoxic substance that can block an NMDA receptor binding site or a NMDA channel. The nontoxic NMDA receptor antagonist may include, for example, dextromethorphan, dextrorphan, ketamine, memantine, pyrroloquinoline quinone, cis-4-(phosphonomethyl)-2-piperidine carboxylic acid, and a physiologically or pharmaceutically acceptable salt thereof (for example, physiologically or pharmaceutically acceptable salts of the anti-inflammatory agent (a), antipyretic analgesic agent (b), and analgesic agent (c)).

Other active ingredients are not particularly limited to a specific one as long as the ingredients do not adversely affect on the analgesic effects and safety of the pharmaceutical preparation of the present invention. For example, other active ingredients may include active ingredients described in Appendix 1 of "Standards of Approval for the manufacture (import) of Antipyretic analgesics" on over-the-counter drugs [Drugs in Japan, OTC Drugs, 2002-03, the 13th edition, Jiho, Inc., pages 92 to 94, issued on Jul. 30, 2001] and active ingredients described in Appendix 1 of "Standards of Approval for the manufacture (import) of Cold medicines" on over-the-counter drugs [Drugs in Japan, OTC Drugs, 2002-03, the 13th edition, Jiho, Inc., pages 1 to 4, issued on Jul. 30, 2001].

In addition to those based on the above-mentioned Standards of Approval, usually, active ingredients suitable for analgesic application may also be added or mixed to or with the pharmaceutical preparation of the present invention as long as the active ingredients have no adverse effect on the analgesic effects and safety of the pharmaceutical preparation of the present invention.

Such an active ingredient may include, for example, a vitamin (e.g., a fat-soluble vitamin such as vitamin A, D, E, K, or U; and a water-soluble vitamin such as vitamin B, C, or P), an antipyretic analgesic anti-inflammatory agent (e.g., a pyrazolone antipyretic analgesic agent such as sulpyrine; a salicylic acid-based agent (a salicylic acid derivative) such as sodium salicylate or aspirin, a fenamic acid-based agent (a fenamic acid derivative) such as flufenamic acid or mefenamic acid, an arylacetic acid-based agent (an arylacetic acid derivative) such as diclofenac sodium or indometacin, a pyrazolidine-based agent (a pyrazolidine derivative) such as phenylbutazone or oxyphenylbutazone, a pyrimidine-based agent (a pyrimidine derivative) such as bucolome, an oxicam-based agent (an oxicam derivative) such as piroxicam, and isopropylantipyrine), an antihistamine (e.g., clemastine fumarate, diphenhydramine hydrochloride, and chlorpheniramine maleate), an antitussive expectorant (for example, an antitussive such as chloperastine, dextromethorphan, or benzonatate; an expectorant, e.g., a mucolytic agent such as bromhexine hydrochloride, L-cysteinehydrochloride, L-cysteinemethylhydrochloride, or acetylcysteine, a mucous repair agent such as carbocisteine, and a mucous lubrication agent such as ambroxol hydrochloride), a bronchodilator or an antasthmatic agent (for example, a $\beta_2$-adrenoceptor stimulant such as pseudoephedorine, ephedrine hydrochloride, methylephedrine hydrochloride, terbutaline hydrochloride, isoproterenol, salbutamol, or terbutaline, a xanthine-based agent (a xanthine derivative) such as theophylline, aminophylline, or proxyphylline, and cromoglicic acid), a local anesthetic agent (for example, an alkamine aminobenzoate-based agent (an alkamine aminobenzoate derivative) such as tetracaine hydrochloride or procaine hydrochloride; a dibucaine-based agent (a dibucaine derivative) such as dibucaine hydrochloride; and a xylidine-based agent (a xylidine derivative) such as bupivacaine hydrochloride, mepivacaine hydrochloride, lidocaine hydrochloride, or ropivacaine hydrochloride), a caffeine compound, an antacid, an amino acid compound, and a crude drug. These active ingredients may be used singly or in combination. Among these ingredients, the local anesthetic agent is often mixed as other active ingredients. The amount of the local anesthetic agent to be mixed in a dose of the pharmaceutical preparation of the present invention may be selected from the range of about 0.1 to 500 mg depending on the species thereof and may usually be about 1 to 400 mg (for example, about 2 to 300 mg). The amount of the local anesthetic agent to be mixed in a dose of the pharmaceutical preparation of the present invention is not particularly limited to a specific one and may be as follows: the amount of tetracaine hydrochloride is about 6 to 80 mg, the amount of procaine hydrochloride is about 10 to 1000 mg, the amount of dibucaine hydrochloride is about 3 to 9 mg, the amount of bupivacaine hydrochloride is about 2.5 to 100 mg, the amount of mepivacaine hydrochloride is about 10 to 500 mg, the amount of lidocaine hydrochloride is about 10 to 300 mg, or the amount of ropivacaine hydrochloride is about 8 to 20 mg.

The pharmaceutical preparation of the present invention can be administered orally or parenterally (for example, transdermally, intravenously, and intramuscularly) according to the symptom (or state) of a patient with a pain. For example, it is preferable that the pharmaceutical preparation of the present invention be orally administered to a patient with a chronic pain, particularly, a neuropathic pain. The preparation suitable for oral administration may be a solid preparation (for example, tablets, pills, microfine particles or powders, granules, powders, hard capsules, soft capsules, troches, and dry syrups) or a non-solid preparation (for example, syrups, liquids and solutions, and suspensions). Incidentally, the pharmaceutical preparation may also include a preparation in which the active ingredient has a controlled releasability (for example, a rapid-release preparation and a sustained release preparation).

The pharmaceutical preparation of the present invention may be obtained by preparing the anti-inflammatory agent (a), the antipyretic analgesic agent (b) and the analgesic agent (c) in combination with a carrier (an additive suitable for a pharmaceutical preparation) with a conventional preparation manner. That is, the pharmaceutical preparation of the present invention may be produced, for example, according to production processes of tablets, granules, powders, hard capsules, soft capsules, troches, dry syrups, syrups, liquids and solutions, and suspensions described in the Japanese Pharmacopoeia. Incidentally, the solid preparation may usually be prepared by using at least one carrier selected from the group consisting of a binder, an excipient, and a disintegrant (particularly, at least an excipient). For example, the granules may be prepared by granulating the active ingredients and carrier component through extrusion granulation or spray granulation, and if necessary, sizing the resultant. The tablets may be produced by mixing the granules and an additive and compression molding tablets from the mixture, and if necessary, coating the tablets for masking the taste or imparting enteric property or prolonged action thereto with per se known methods. The capsules may be prepared by filling granules in a capsule. The liquids and solutions may be prepared, depending on the dosage form, by mixing the active ingredients and a liquid carrier component (e.g., water), and if necessary, an additive (for example, an emulsifier, a dispersing agent or a suspending agent, a preservative, a stabilizer, a corrigent, and a pH adjusting agent or a buffer). If necessary, the liquids and solutions are sterilized.

The above-mentioned carrier (additive for the preparation) may include an additive commonly used for manufacturing a pharmaceutical preparation having the above-mentioned dosage form. For example, the carrier may include an excipient, a binder, a disintegrant, a lubricant, and a coating agent each of which is listed in the Japanese Pharmacopoeia and "Encyclopedia of Pharmaceutical Excipients (Iyakuhin Tenkabutsu Jiten)" (Yakuji Nippo Ltd., the second issue, issued on Mar. 25, 2002).

Among the carrier components or additives, the excipient may include a starch such as a corn starch, a polysaccharide such as a crystalline cellulose; a saccharide such as lactose, white soft sugar or refined sugar, glucose, mannitol, or sorbitol; and others. The binder may include a polysaccharide such as a pregelatinized starch, agar, gum acacia (or gum arabic), or dextrin; a synthetic polymer such as a polyvinylpyrrolidone, a polyvinyl alcohol, a carboxyvinyl polymer, or a polylactic acid; a cellulose ether such as a methyl cellulose, an ethyl cellulose, a carboxymethyl cellulose (CMC) sodium, a hydroxyethyl cellulose, a hydroxypropyl cellulose, or a hydroxypropylmethyl cellulose; and others. The disintegrant may include calcium carbonate, a carboxymethyl cellulose calcium (a carmellose calcium), a crosslinked povidone, a low-substituted hydroxypropyl cellulose, and others. The lubricant may include, for example, a talc, magnesium stearate, and a polyethylene glycol 6000. Moreover, a disintegrant aid, a lipid (for example, a fat and oil such as a hydrogenated vegetable oil, and a phospholipid), a macrogol, a corrigent or a masking agent, a coloring agent, an aromatic substance, and others may be used.

The coating agent which may be used may include, for example, a saccharide, a cellulose derivative such as an ethyl cellulose or a hydroxymethyl cellulose, a polyoxyethylene glycol, a cellulose acetate phthalate, a hydroxypropylmethyl cellulose phthalate, and eudragit (e.g., a methacrylic acid-acrylic acid copolymer). The coating agent may be an enteric component such as a hydroxypropylmethyl cellulose phthalate or a gastric soluble component comprising a polymer (e.g., eudragit) containing a basic component such as a dialkylaminoalkyl(meth)acrylate.

The pharmaceutical preparation of the present invention is effective in treating or alleviating pain. Although the pain is not particularly limited to a specific one, the pain is roughly divided into acute pain and chronic pain. The pain is also divided into four following categories according to the causes: nociceptive, inflammatory, neuropathic, and psychogenic pains. The pharmaceutical preparation of the present invention is effective for the chronic pain among others, in particular, for a neuropathic pain accompanied by a disorder of the nerve itself. Further, the pharmaceutical preparation of the present invention is effective for carcinomatous pain, post-herpes-zoster neuralgia, post-thoracotomy pain, trigeminal neuralgia, phantom limb pain, causalgia, diabetic neuropathic pain, injury or amputation of limb, and others, each of which is a disease with a neuropathic pain.

Furthermore, the pharmaceutical preparation of the present invention has an excellent enough analgesic effect, also an excellent analgesic effect on a neuropathic pain, compared with an analgesic effect of the opioid analgesic agent (analgesic agent (c)) alone.

Neither the propionic acid-derived nonsteroidal anti-inflammatory agent nor the non-pyrazolone antipyretic analgesic agent has an analgesic effect on a neuropathic pain. However, in a combination use with the opioid analgesic agent, a combination of the propionic acid-derived nonsteroidal anti-inflammatory agent and the non-pyrazolone antipyretic analgesic agent serves as the potentiator for the analgesic effect of the opioid analgesic agent. Thus the pharmaceutical preparation of the present invention shows an excellent analgesic effect on the neuropathic pain.

The pharmaceutical preparation of the present invention is usually administered (for example, orally administered) in one to several dose(s) a day. The dose thereof may suitably be adjusted depending on the age, body weight, symptom, and others of a subject [human beings (including infants), non-human beings (e.g., mammals such as bovines, monkeys, dogs, or cats)].

In the pharmaceutical preparation of the present invention, the anti-inflammatory agent (a) (e.g., ibuprofen) is preferably used so that the dose of the anti-inflammatory agent (a) (e.g., ibuprofen) can be about 100 to 1000 mg/day, preferably about 200 to 800 mg/day, and more preferably about 300 to 600 mg/day in adult.

Moreover, in the pharmaceutical preparation of the present invention, the amount of the antipyretic analgesic agent (b) (e.g., acetaminophen) may be adjusted depending on the used amount of the anti-inflammatory agent (a) (e.g., ibuprofen). The antipyretic analgesic agent (b) (e.g., acetaminophen) may be used in a proportion of about 40 to 60 parts by weight, preferably about 40 to 50 parts by weight, relative to 100 parts by weight of the anti-inflammatory agent (a) (e.g., ibuprofen).

Further, in the pharmaceutical preparation of the present invention, the amount of analgesic agent (c) (e.g., at least one member selected from the group consisting of codeine phosphate and dihydrocodeine phosphate) may be adjusted depending on the used amount of the anti-inflammatory agent (a) (e.g., ibuprofen). The analgesic agent (c) (e.g., at least one member selected from the group consisting of codeine phosphate and dihydrocodeine phosphate) may be mixed in a proportion of about 1 to 500 parts by weight, preferably about 1 to 100 parts by weight, relative to 100 parts by weight of the anti-inflammatory agent (a) (e.g., ibuprofen).

The pharmaceutical preparation of the present invention may contain a local anesthetic agent in addition to the anti-inflammatory agent (a), the antipyretic analgesic agent (b), and the analgesic agent (c). The used amount of the local anesthetic agent may be adjusted depending on the used amount of the anti-inflammatory agent (a) (e.g., ibuprofen). The local anesthetic agent may be used in a proportion of about 0.1 to 200 parts by weight, preferably about 0.5 to 100 parts by weight (e.g., about 1 to 70 parts by weight), relative to 100 parts by weight of the anti-inflammatory agent (a) (e.g., ibuprofen).

INDUSTRIAL APPLICABILITY

The pharmaceutical preparation of the present invention is effective for treating or alleviating a pain such as acute pain or chronic pain (for example, nociceptive, inflammatory, neuropathic, and psychogenic pains). The pharmaceutical preparation of the present invention also has a beneficial effect on a neuropathic pain accompanied by a disorder of the nerve itself or a disease resulting from a neuropathic pain (for example, carcinomatous pain, postherpetic neuralgia, post-thoracotomy pain, trigeminal neuralgia, phantom limb pain, causalgia, diabetic neuropathic pain, and injury or amputation of limb).

EXAMPLES

Hereinafter, the following examples are intended to describe this invention in further detail and should by no means be interpreted as defining the scope of the invention.

Test Example 1

Dihydrocodeine Phosphate

Analgesic Effect on Chronic Constriction Injury (CCI) Model

The three following agents (1) to (3) were used as test agents: (1) a combination agent containing ibuprofen and acetaminophen in a weight ratio of ibuprofen:acetaminophen which was 1:0.5 (hereinafter, sometimes referred to as the "two-component combination agent"; Comparative Example 1), (2) a combination agent containing ibuprofen, acetaminophen, and dihydrocodeine phosphate in a weight ratio of ibuprofen:acetaminophen:dihydrocodeine phosphate which was 1:0.5:0.06 (hereinafter, sometimes referred to as the "three-component combination agent"; Example 1), and (3) dihydrocodeine phosphate (DCP) alone (Comparative Example 2). The analgesic effects of these agents were tested using Plantar test in accordance with the method of Bennett and Xie [Bennett G J and Xie Y-K: A peripheral mononeuropathy in rat that produces disorders of pain sensation like those seen in man. Pain, 33 (1988) 87-107]. Incidentally, a group administered 1% carboxymethyl cellulose sodium (1% CMC—Na) alone was used as a control group.

Specifically, CCI model rats were made in accordance with the method of Bennett et al. and the method of Yamamoto et al. [Yamamoto T and Yaksh T L: Spinal pharmacology of thermal hyperesthesia induced by incomplete ligation of sciatic nerve. Anesthesiology 75, 817-826 (1991)]. Then each test agent was orally administered at a dose of 5 mL/kg to the rats. The Plantar test was performed every 30 minutes from the start of the administration to 3 hours after the administration to measure a pseudo pain response-related withdrawal latency (second) of the rat hind limb which had undergone C+CI. The results are shown in Table 1. Incidentally, in FIG. 1, white bars, black bars, horizontal-striped bars, and vertical-striped bars correspond to the control group, Comparative Example 1, Comparative Example 2, and Example 1, respectively.

TABLE 1

Pseudo Pain Response-Related Withdrawal Latency in Rats (unit: second)

|  | Before Administration | After 30 minutes | After 1 hour | After 1.5 hours | After 2 hours | After 2.5 hours | After 3 hours |
|---|---|---|---|---|---|---|---|
| Control Group (CMC-Na administration) | 7.3 | 7.4 | 6.8 | 6.7 | 6.2 | 6.5 | 5.3 |
| Comparative Example 1 (2-component combination agent administration) | 7 | 8 | 6.1 | 7.5 | 7.6 | 7.1 | 7.4 |
| Comparative Example 2 (DCP administration) | 6.5 | 11.6 | 9.8 | 6.8 | 6.9 | 8.1 | 8.9 |
| Example 1 (3-component combination agent administration) | 7 | 15.9 | 11.6 | 14 | 14.6 | 15.3 | 15.4 |

As apparent from Table 1 and FIG. 1, in the case of the administration of the two-component combination agent, no analgesic effect on neuropathic pain was observed. In the case of the administration of dihydrocodeine phosphate alone, an analgesic effect similar to the case of the two-component combination agent or only slight analgesic effect was recognized. In contrast, in the case of the three-component combination agent, in which dihydrocodeine phosphate had been added to the two-component combination agent, an excellent analgesic effect was observed compared with the administration of dihydrocodeine phosphate alone.

Preparation Example 1

Formulation per tablet (total amount 140 mg): ibuprofen 75 mg, acetaminophen 32.5 mg, codeine phosphate 8 mg, corn starch 17.5 mg, and a low-substituted hydroxypropylcellulose 7 mg According to the above-mentioned formulation, tablets to be taken as two tablets at a time were produced in accordance with a known manner described in General Rules for Preparations of Japanese Pharmacopoeia.

Preparation Example 2

Formulation per tablet (total amount 140 mg): ibuprofen 60 mg, acetaminophen 30 mg, dihydrocodeine phosphate 4 mg, corn starch 39 mg, and a low-substituted hydroxypropylcellulose 7 mg According to the above-mentioned formulation, tablets to be taken as two tablets at a time were produced in accordance with a known manner described in General Rules for Preparations of Japanese Pharmacopoeia.

Preparation Example 3

Formulation per capsule (total amount 170 mg): ibuprofen 75 mg, acetaminophen 32.5 mg, codeine phosphate 16 mg, corn starch 44.5 mg, and magnesium stearate 2 mg According to the above-mentioned formulation, capsules to be taken as two capsules at a time were produced in accordance with a known manner described in General Rules for Preparations of Japanese Pharmacopoeia.

Preparation Example 4

Formulation per capsule (total amount 170 mg): ibuprofen 60 mg, acetaminophen 30 mg, dihydrocodeine phosphate 4 mg, corn starch 74 mg, and magnesium stearate 2 mg According to the above-mentioned formulation, capsules to be taken as two capsules at a time were produced in accordance with a known manner described in General Rules for Preparations of Japanese Pharmacopoeia.

Preparation Example 5

Formulation per package of granules (total amount 640 mg): ibuprofen 150 mg, acetaminophen 65 mg, codeine phosphate 16 mg, lactose 154 mg, crystalline cellulose 200 mg, corn starch 50 mg, and a low-substituted hydroxypropylcellulose 5 mg According to the above-mentioned formulation, granules to be taken as one package at a time were produced in accordance with a known manner described in General Rules for Preparations of Japanese Pharmacopoeia.

Preparation Example 6

Formulation per package of granules (total amount 630 mg): ibuprofen 120 mg, acetaminophen 30 mg, dihydrocodeine phosphate 8 mg, lactose 200 mg, crystalline cellulose 267 mg, and a low-substituted hydroxypropylcellulose 5 mg According to the above-mentioned formulation, granules to be taken as one package at a time were produced in accordance with a known manner described in General Rules for Preparations of Japanese Pharmacopoeia.

The invention claimed is:

1. A pharmaceutical preparation containing a propionic acid-derived nonsteroidal anti-inflammatory agent, a non-pyrazolone antipyretic analgesic agent, and an opioid analgesic agent, which alleviates or treats a neuropathic pain, wherein
the proportion of the non-pyrazolone antipyretic analgesic agent is 20 to 80 parts by weight relative to 100 parts by weight of the propionic acid-derived nonsteroidal anti-inflammatory agent,
the proportion of the opioid analgesic agent is 1 to 50 parts by weight relative to 100 parts by weight of the propionic acid-derived nonsteroidal anti-inflammatory agent, the dose of the propionic acid-derived nonsteroidal anti-inflammatory agent is about 100 to 1000 mg/day for an adult, and the propionic acid-derived nonsteroidal anti-inflammatory agent comprises ibuprofen, the non-pyrazolone antipyretic analgesic agent comprises acetaminophen, and the opioid analgesic agent comprises at least one member selected from the group consisting of codeine phosphate and dihydrocodeine phosphate.

2. A pharmaceutical preparation according to claim 1, wherein the proportion of the opioid analgesic agent is 1 to 1000 parts by weight relative to 100 parts by weight of the non-pyrazolone antipyretic analgesic agent.

3. A pharmaceutical preparation according to claim 1, which is substantially free from a nontoxic N-methyl-D-aspartate receptor antagonist, wherein the proportion of the non-pyrazolone antipyretic analgesic agent and that of the opioid analgesic agent are 30 to 70 parts by weight and 3 to 50 parts by weight, respectively, relative to 100 parts by weight of the propionic acid-derived nonsteroidal anti-inflammatory agent.

4. A pharmaceutical preparation for alleviating or treating a neuropathic pain, which is substantially free from a nontoxic N-methyl-D-aspartate receptor antagonist and contains a propionic acid-derived nonsteroidal anti-inflammatory agent, a non-pyrazolone antipyretic analgesic agent, and an opioid analgesic agent, wherein
the proportion of the non-pyrazolone antipyretic analgesic agent is 40 to 60 parts by weight relative to 100 parts by weight of the propionic acid-derived nonsteroidal anti-inflammatory agent, the proportion of the opioid analgesic agent is 3 to 40 parts by weight relative to 100 parts by weight of the propionic acid-derived nonsteroidal anti-inflammatory agent, the dose of the propionic acid-derived nonsteroidal anti-inflammatory agent is about 100 to 1000 mg/day for an adult, and the propionic acid-derived nonsteroidal anti-inflammatory agent comprises ibuprofen, the non-pyrazolone antipyretic analgesic agent comprises acetaminophen, and the opioid analgesic agent comprises at least one member selected from the group consisting of codeine phosphate and dihydrocodeine phosphate.

5. A method for alleviating or treating a neuropathic pain by administering the pharmaceutical preparation recited in claim 1.

* * * * *